(12) United States Patent
Ritchey et al.

(10) Patent No.: US 9,301,767 B2
(45) Date of Patent: Apr. 5, 2016

(54) INSTRUMENT FOR FRACTURE FRAGMENT ALIGNMENT AND STABILIZATION

(75) Inventors: Nicholas S. Ritchey, Collierville, TN (US); Thomas A. Russell, Eads, TN (US); Roy W. Sanders, Tampa, TN (US)

(73) Assignee: Smith & Nephew, Inc., Memphis, TN (US)

(*) Notice: Subject to any disclaimer, the term of this patent is extended or adjusted under 35 U.S.C. 154(b) by 616 days.

(21) Appl. No.: 13/562,944

(22) Filed: Jul. 31, 2012

(65) Prior Publication Data

US 2013/0006258 A1    Jan. 3, 2013

Related U.S. Application Data

(63) Continuation of application No. 11/816,909, filed as application No. PCT/US2006/006178 on Feb. 22, 2006, now Pat. No. 8,257,361.

(60) Provisional application No. 60/655,100, filed on Feb. 22, 2005.

(51) Int. Cl.
*A61B 17/56* (2006.01)
*A61B 17/17* (2006.01)
*A61B 17/00* (2006.01)

(52) U.S. Cl.
CPC ... *A61B 17/1725* (2013.01); *A61B 2017/00902* (2013.01); *A61B 2017/00915* (2013.01)

(58) Field of Classification Search
CPC .................. A61B 17/56; A61B 2017/00915
USPC .................. 606/64, 86 R, 87–89, 96–98
See application file for complete search history.

(56) References Cited

U.S. PATENT DOCUMENTS

| | | | | |
|---|---|---|---|---|
| 4,865,025 | A * | 9/1989 | Buzzi et al. | 606/96 |
| 4,976,713 | A * | 12/1990 | Landanger et al. | 606/62 |
| 6,039,742 | A * | 3/2000 | Krettek et al. | 606/96 |
| 6,093,192 | A * | 7/2000 | Abel | 606/98 |
| 6,214,013 | B1 * | 4/2001 | Lambrecht et al. | 606/96 |
| 6,514,253 | B1 * | 2/2003 | Yao | 606/53 |
| 6,702,823 | B2 * | 3/2004 | Iaia | 606/98 |
| 2003/0074005 | A1 * | 4/2003 | Roth et al. | 606/99 |
| 2003/0149486 | A1 * | 8/2003 | Huebner | 623/19.11 |
| 2004/0215204 | A1 * | 10/2004 | Davison et al. | 606/98 |

* cited by examiner

*Primary Examiner* — Christopher Beccia
(74) *Attorney, Agent, or Firm* — Taft Stettinius & Hollister LLP

(57) ABSTRACT

An instrument for locating an axis of a blocking screw is disclosed. The instrument is applicable for a retrograde installation of a femoral intramedullary device or an antegrade installation of a tibial intramedullary device. The instrument includes a drill jig with a radiolucent frame portion and a mounting portion. The mounting portion is adapted to connect to an intramedullary device, and the frame portion has at least one aperture for locating the axis of the blocking screw. The drill jig is adjustable to locate the aperture in a longitudinal or rotational direction relative to the intramedullary device.

28 Claims, 11 Drawing Sheets

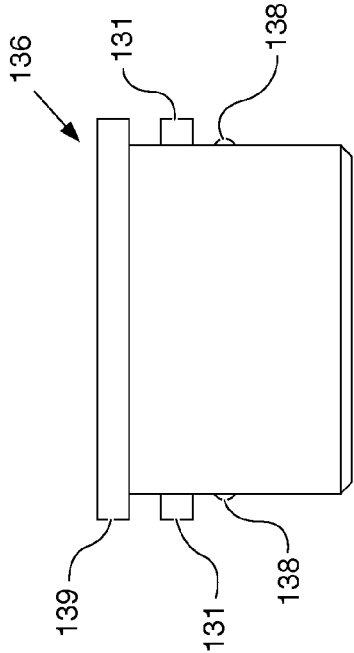
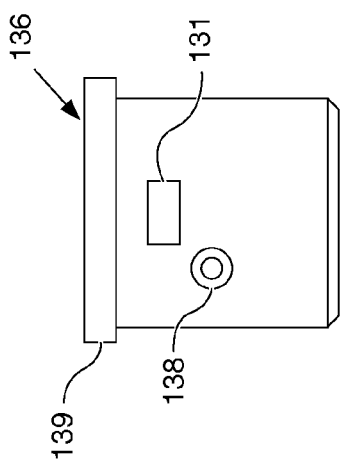
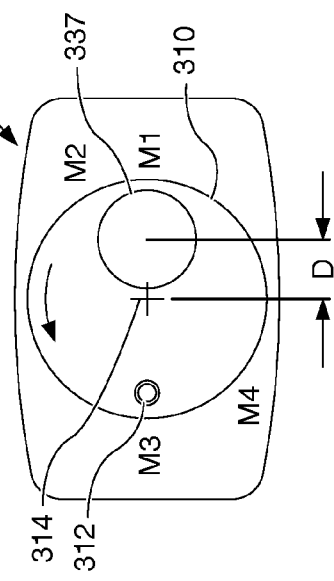
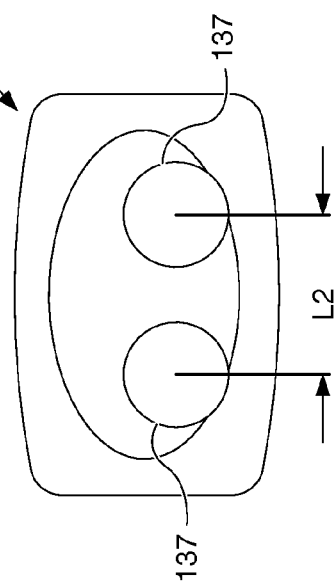
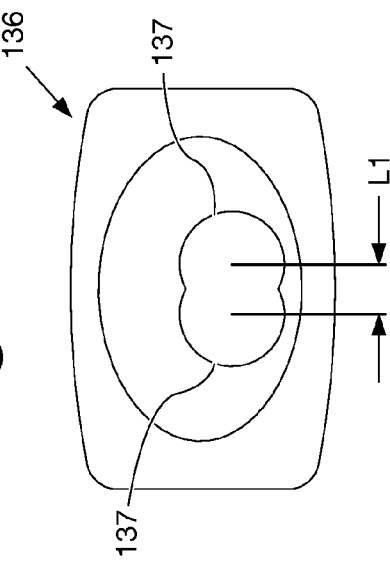

INSTRUMENT FOR FRACTURE FRAGMENT ALIGNMENT AND STABILIZATION

CROSS-REFERENCE TO RELATED APPLICATIONS

This application is a continuation of U.S. application Ser. No. 11/816,909 filed Aug. 22, 2007, which is a National Phase of International Application No. PCT/US2006/006178, filed Feb. 22, 2006. This application claims the benefit of U.S. Provisional Application No. 60/655,100, filed Feb. 22, 2005. The disclosure of each prior application is incorporated by reference in its entirety.

STATEMENT REGARDING FEDERALLY SPONSORED RESEARCH OR DEVELOPMENT.

Not Applicable.

APPENDIX

Not Applicable.

BACKGROUND OF THE INVENTION

1. Field of the Invention

This invention relates generally to intramedullary devices and, more particularly, to an instrument for targeting blocking screws relative to an intramedullary device.

2. Related Art

Blocking screws are often used to supplement the installation of an intramedullary nail. There are three primary reasons for the use of blocking screws. First, blocking screws may be used to direct the path of an intramedullary nail. The nailing of metaphyseal fractures with short proximal or distal fractures is often associated with an increase in frontal and sagittal plane malalignment. As an example, the malalignment may be a result of an incorrect entry site. The blocking screw can be used to direct the path of the nail to correct this type of malalignment.

Second, blocking screws may be used to stabilize an intramedullary nail. Instability may be caused by the difference in size between the implant and the medullary cavity. If the difference is significant, the intramedullary nail will not contact the metaphyseal cortex and will translate along the interlocking screws. The blocking screws can be placed in strategic locations to functionally decrease the -width of the metaphyseal medullar cavity and prevent the nail from migrating.

Third, blocking screws may be used to correct a deformity, in other words, the blocking screws are placed in the metaphyseal region in such a way as to direct the path of the intramedullary nail to correct the bone deformity.

Presently, a surgeon uses a free-hand technique or a metal jig for the insertion of blocking screws. The free-hand technique is prone to errors as the surgeon does not have an effective guide for the placement of the blocking screw. The metal jig is also undesirable because it does not allow the surgeon to verify the location of the blocking screw prior to insertion. The metal jig interferes with X-rays and image enhancers, thereby preventing verification of the blocking screw placement prior to installation.

Additionally, blocking screws may be used to align fracture fragments or stabilize fracture fragments. However, it is often difficult to correctly place the fragments prior to interlocking of the intramedullary nail or placement of the blocking screw. Typically a second surgeon or nurse is required to aid in positioning of the fracture fragments while the surgeon performs the procedure. Additional personnel increase the cost of the procedure and the amount of time required to perform the procedure. Moreover, due to the limited size of most operating rooms, additional personnel tend to crowd the operating room and decrease operating room efficiency.

There remains a need in the art for an instrument to guide or target the accurate placement of blocking screws. There also remains a need in the art for a radiolucent instrument that can be used to verify the placement of a blocking screw prior to insertion. Finally, there remains a need in the art for a device which aids a single surgeon in the proper alignment of fracture fragments.

SUMMARY OF THE INVENTION

It is in view of the above problems that the present invention was developed. The invention is an instrument for locating an axis of a blocking screw. The instrument is applicable for a retrograde installation of a femoral intramedullary device or an antegrade installation of a tibial intramedullary device. The instrument has a frame portion and a mounting portion. The instrument has at least one aperture for locating the axis of one or more blocking screws.

In one aspect of the invention, the instrument is adjustable relative to the intramedullary device in order to locate one or more blocking screws at preselected location. Adjustment of the instrument is accomplished by adjusting the frame portion or by adjusting the mounting portion. Additionally, the instrument is rotatable relative to the intramedullary device in order to locate one or more blocking screws at preselected location.

In another aspect of the invention, at least a portion of the instrument is radiolucent. For example, the frame portion and/or the mounting portion are radiolucent. This allows a user to verify the location of the blocking screw prior to insertion.

In yet another aspect of the invention, the instrument may include a fracture alignment device for the alignment and stabilization of fracture fragments. The fracture alignment device aids a single user in the proper alignment and/or placement of fracture fragments.

The invention has several advantages over prior devices and techniques. First, the invention has features that allow the surgeon to accurately place blocking screws in relation to the ultimate position of the intramedullary nail and locking screws. Second, the instrument has features that allow the surgeon or other user to verify that the blocking screws have been properly located prior to insertion. Third, the instrument may include features that allow the surgeon to manipulate and place bone fragments for correct alignment.

Thus, in furtherance of the above goals and advantages, the present invention is, briefly, an instrument for locating an axis of a blocking screw. The instrument includes a drill jig with a radiolucent frame portion and a mounting portion. The mounting portion is adapted to connect to an intramedullary device, and the frame portion has at least one aperture for locating the axis of the blocking screw. The drill jig is adjustable to locate the aperture in a longitudinal direction relative to the intramedullary device. The mounting portion is adjustable in a first embodiment, and the frame portion is adjustable in a second embodiment.

Further, the invention is, briefly, an instrument for locating an axis of a blocking screw. The instrument includes a frame, a mount operatively connected to the frame and adapted to connect to an intramedullary device, a pilot member removably attached to the frame, and a cartridge slidably connected to the pilot member. The cartridge has at least one aperture for locating the axis of the blocking screw. The cartridge is moved relative to the pilot member to select the axis of the blocking screw.

Further, the invention is, briefly, a drill jig assembly for locating an axis of a blocking screw. The drill jig assembly includes a drop, a drill guide removably attached to the drop and adapted to operatively connect to an intramedullary device, a blocking screw attachment removably attached to the drop, and a blocking screw cartridge. The blocking screw attachment has a pair of tracks, and the blocking screw cartridge is slidably connected to the pair of tracks. The blocking screw cartridge has at least one aperture adapted to receive an outer drill sleeve. The blocking screw cartridge is adjusted along the pair of tracks to locate the aperture at a selected location for the axis of the blocking screw.

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings:

FIG. 7 is a side view of a cartridge in a first embodiment;

FIG. 8 is a front view of the cartridge shown in FIG. 7;

FIG. 9 is a top view of the cartridge shown in FIG. 7 with a first hole spacing;

FIG. 10 is a top view of the cartridge shown in FIG. 7 with a second hole spacing;

FIG. 11 is a top view of a cartridge in a second embodiment;

DETAILED DESCRIPTION OF THE PREFERRED EMBODIMENTS

Figure 1:
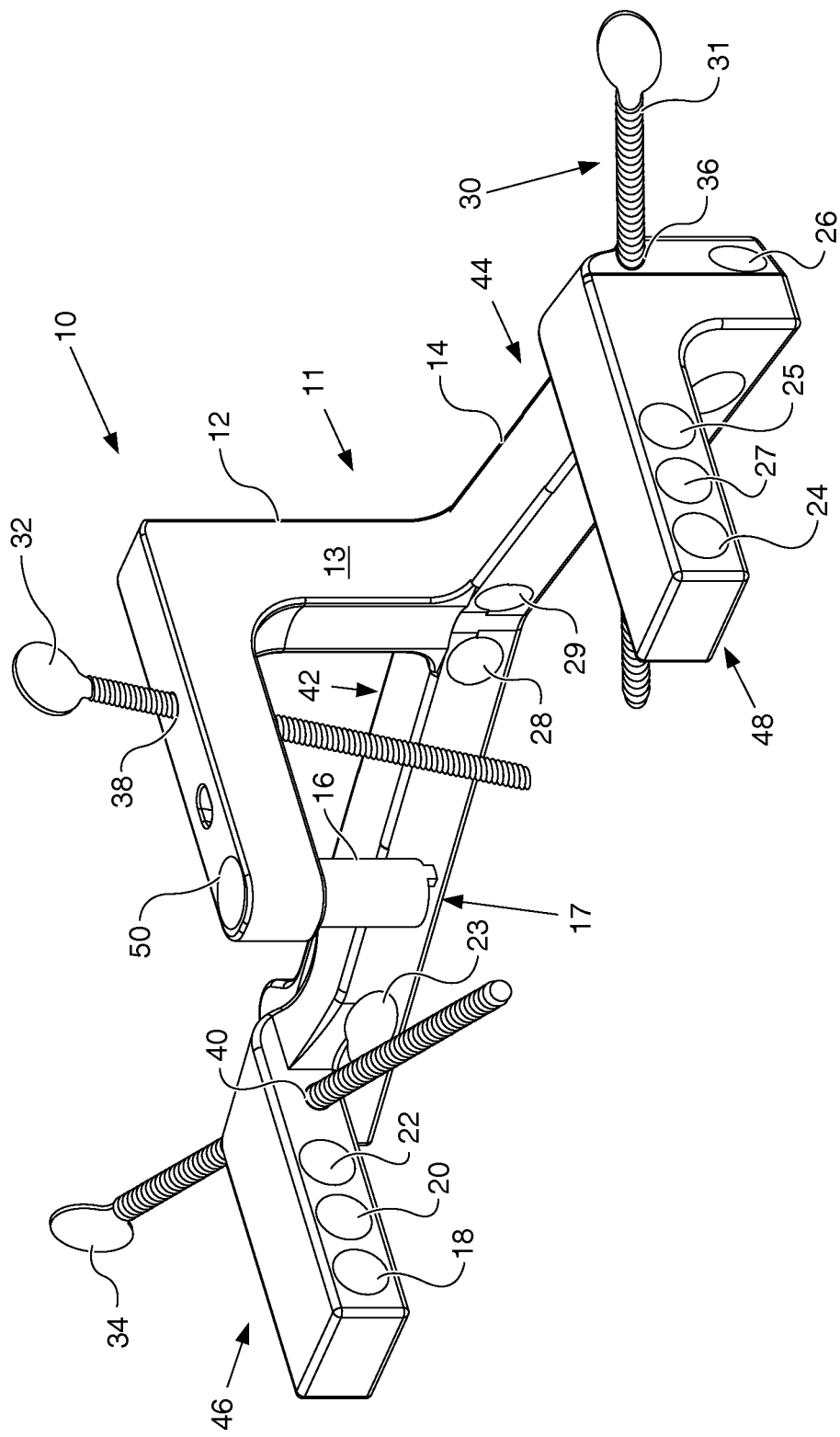
FIG. 1 is a perspective view of a first embodiment of an instrument for locating an axis of a blocking screw.
Figure 2:
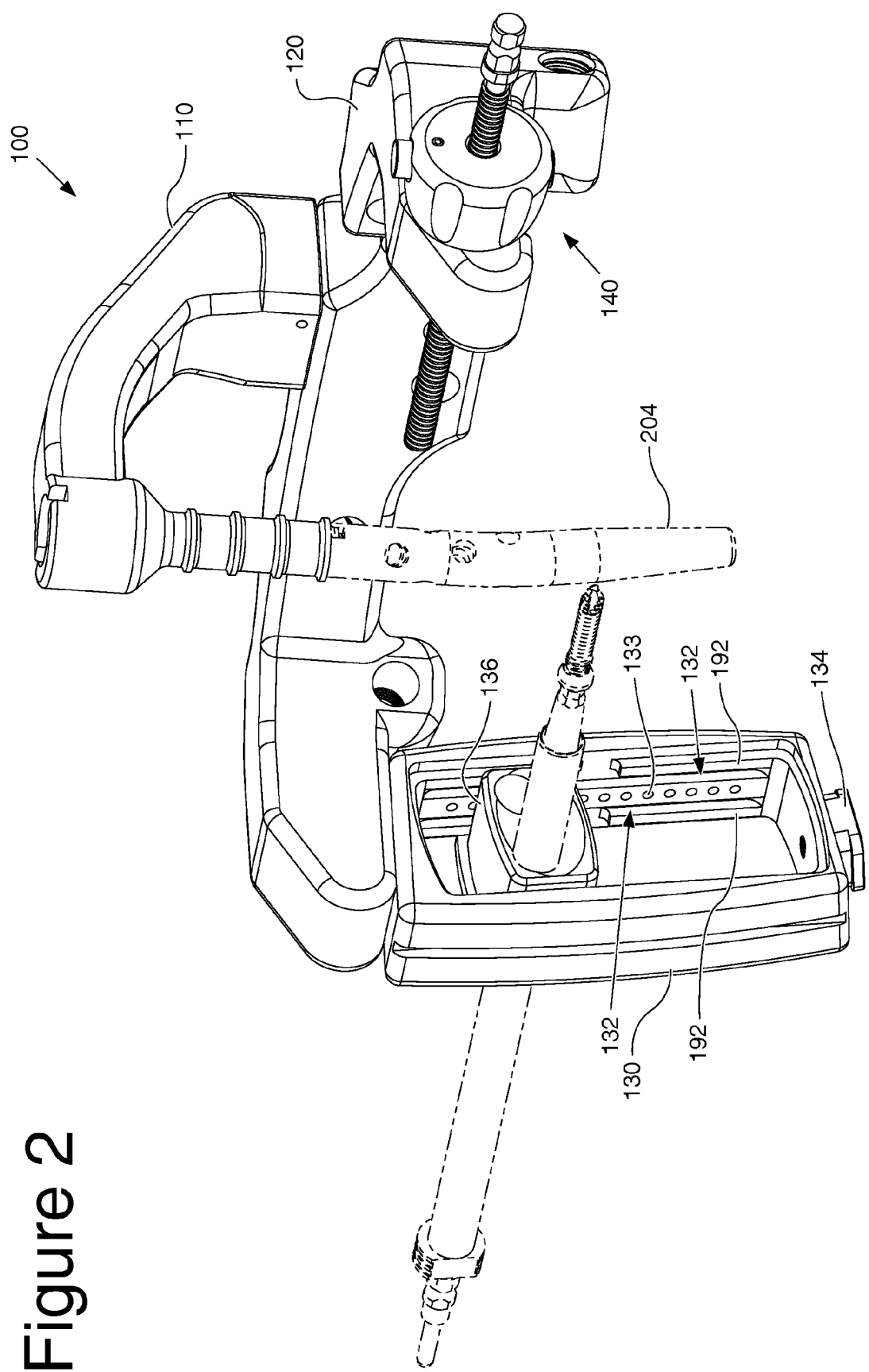
FIG. 2 is perspective view of a second embodiment of an instrument for locating an axis of a blocking screw.

Referring to the accompanying drawings in which like reference numbers indicate like elements, FIG. 1 illustrates an instrument 10, or drill guide assembly, for locating an axis of a blocking screw. The instrument 10 is applicable for a retrograde installation of an intramedullary device into a femur or an antegrade installation of an intramedullary device into a tibia. The instrument 10 includes a drill jig 11 having a radiolucent frame portion 14 and a mounting portion 12. The mounting portion 12 may also be referred to as a drill guide, and the frame portion 14 may also be referred to as a drop. The frame portion 14 is made of plastic, a composite material, or other radiolucent material. In the embodiment depicted in FIG. 1, the mounting portion 12 is integral with the frame portion 14. However, those skilled in the art would understand that the mounting portion 12 and the frame portion 14 may be separate components but capable of being coupled together. The mounting portion 12 is adapted to connect to an intramedullary device 204 (best seen in FIG. 4), such as a trial or a nail, to a reduction tool, or to an awl. In the depicted embodiment, a barrel 16 is connected to the mounting portion 12, and the barrel 16 connects to the intramedullary device at a first end 17. The barrel 16 is hollow, and a fastener (not shown) may be inserted into a fastener hole 50 to secure the intramedullary device to the mounting portion 12. The mounting portion 12 also has a neck 13 which extends in a generally perpendicular direction from the frame portion 14.

The frame portion 14 has a first leg 42 and a second leg 44. In the embodiment depicted in FIG. 1, the second leg 44 extends at an angle relative to the first leg 42. A first protrusion 46 extends from the first leg 42, and a second protrusion 48 extends from the second leg 44. In the embodiment depicted in FIG. 1, the second protrusion 48 is parallel to the first protrusion 46.

The frame portion 14 also has a hole or aperture for locating an axis of a blocking screw, in the embodiment depicted in FIG. 1, the frame portion 14 has a first blocking screw hole 18, a second blocking screw hole 22, a third blocking screw hole 24, a fourth blocking screw hole 25, a fifth blocking screw hole 28, and a sixth blocking screw hole 29. While six blocking screw holes are shown, those skilled in the art would understand that a greater or lesser number of holes may be provided. The first blocking screw hole 18 and the second blocking screw hole 22 are located in the first protrusion 46, and the third blocking screw hole 24 and the fourth blocking screw hole 25 are located in the second protrusion 48. The fifth blocking screw hole 28 is located in the first leg 42, and the sixth blocking screw hole 29 is located in the second leg 44.

In some embodiments, the frame portion 14 may also include nail targeting holes which may be used to target an axis of a screw for locking the intramedullary device to the bone. In the embodiment depicted in FIG. 1, the frame portion 14 has a first nail targeting hole 20, a second nail targeting hole 23, a third nail targeting hole 26, and a fourth nail targeting hole 27. While four nail targeting holes are shown, those skilled in the art would understand that a greater or lesser number of holes may be provided. The first nail targeting hole 20 is located in the first protrusion 46, and the fourth nail targeting hole 27 is located in the second protrusion 48. The second nail targeting hole 23 is located in the first leg 42, and the third nail targeting hole 26 is located in the second leg 44.

The frame portion 14 or the mounting portion 12 may be adjustable in a longitudinal direction relative to the intramedullary device in order to locate the axis of the blocking screw. In other words, the frame portion 14 or the mounting portion 12 may be adjustable in a longitudinal direction along an imaginary axis of the intramedullary device in order to locate the axis of the blocking screw. As an example, the barrel 16 may be available in different lengths or extendable to allow for adjustment of the mounting portion 12. If the barrel 16 is available in different lengths, then the barrel can be removed and replaced by a second barrel having a length different than the first barrel. Alternatively, the barrel 16 may be extended or collapsed to move the frame portion 14 relative to the intramedullary device, in this manner, the position of the hole or aperture for locating the axis of the blocking screw relative to the intramedullary device may be adjusted. As another example, the neck 13 may be available in different lengths or extendable to adjust the relative position of the blocking screw axis.

Optionally, the instrument 10 may include a fracture alignment device 30. The fracture alignment device 30 is used in conjunction with the frame portion 14 to rotate and/or translate bone fragments. In the embodiment depicted in FIG. 1, there are three fracture alignment devices 31, 32, 34, but those skilled in the art would understand that a greater or lesser number of devices may be used. Each fracture alignment device 31, 32, 34 is operatively connected to the drill jig 11. In the embodiment depicted in FIG. 1, each fracture alignment device 31, 32, 34 threadingly engages the drill jig 11. Accordingly, the drill jig 11 includes a first mounting hole 36, a second mounting hole 38, and a third mounting hole 40. Each fracture alignment device 31, 32, 34 corresponds to the respective mounting hole 36, 38, 40. Each fracture alignment device 31, 32, 34 may have a predefined angle relative to the barrel 16, or each fracture alignment device 31, 32, 34 may swivel such that the surgeon may choose an angle relative to the drill jig 11.

FIGS. 2-18 depict a second embodiment of the instrument, generally indicated by numeral reference 100. The instrument 100 is used to, among other things, locate an axis of a blocking screw 210 relative to an intramedullary device 204, such as a trial or a nail. The instrument 100 may also be used to target an axis of a screw used to lock the intramedullary device 204 to a bone.

The instrument, or drill guide assembly, 100 includes a frame 120, a mount 110, a pilot member 130, and a cartridge 136. Optionally, the instrument 100 may also have a fracture alignment device 140. In the depicted embodiments, the mount 110 is removably attached to the frame 120. However, those skilled in the art would understand that the mount 110 and the frame 120 may be integrally formed together. When the mount 110 and the frame 120 are coupled together, the combination may be referred to as a drill jig 105 (best seen in FIG. 5). Further, the mount 110 also may be termed a drill guide or simply a guide, and the frame 120 also may be termed a drop or a base.

Figure 3:
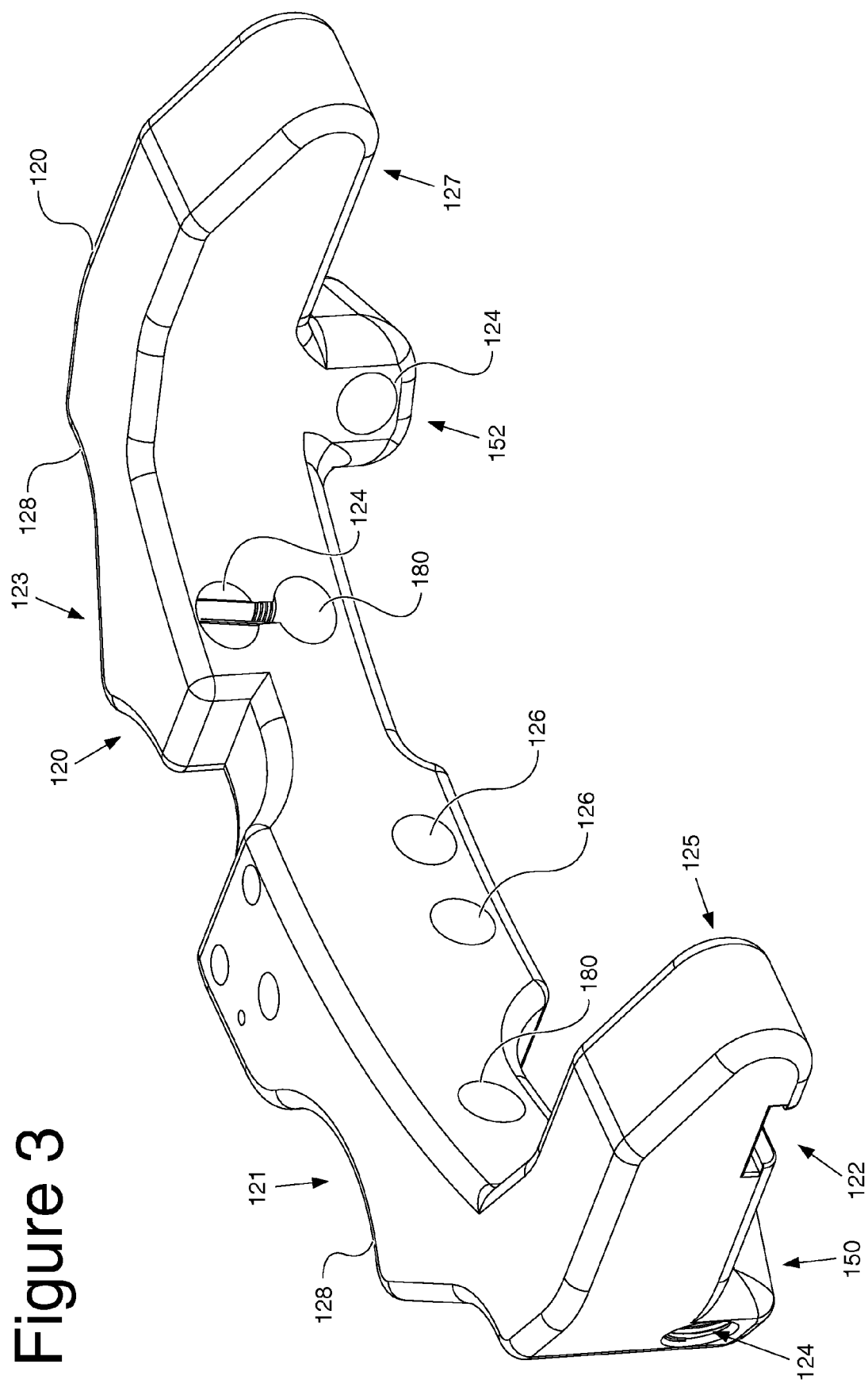
FIG. 3 is a perspective view of a frame.

FIG. 3 illustrates the frame 120. The frame 120 is made of plastic, a composite material, or other radiolucent material. The frame 120 has a first leg 121 and a second leg 123. In the embodiment depicted in FIG. 3, the second leg 123 and the first leg 121 are arcuate and form one continuous curve. Additionally, each leg 121, 123 may include scalloped or cut out portions 128 to provide added clearance and to save weight. A first protrusion 125 extends from the first leg 121, and a second protrusion 127 extends from the second leg 123. In the embodiment depicted in FIG. 3, the second protrusion 127 is parallel to the first protrusion 125.

The frame 120 includes at least one channel 122 for mounting the pilot member 130. In the depicted embodiments, each protrusion 125, 127 includes a channel 122. In some embodiments, additional channels 122 may be located on the legs 121, 123 or at the location where the first leg 121 meets the second leg 123.

In some embodiments, the frame 120 includes at least one mounting hole 124 for receiving the fracture alignment device 140. In the embodiment depicted in FIG. 3, the frame 120 includes a third protrusion 150 and a fourth protrusion 152 located at the respective end portion of each leg 121, 123, and each of the third protrusion 150 and the fourth protrusion 152 includes the mounting hole 124.

The frame 120 may include one or more holes or apertures for locating an axis of a blocking screw. As an example, the embodiment depicted in FIG. 3 includes blocking screw locating holes 126, with one of the blocking screw holes 126 located in each leg 121, 123. The frame 120 may also include nail target holes 180 which may be used to target an axis of a screw for locking the intramedullary device to the bone, in the embodiment depicted in FIG. 3, the frame 120 has two nail targeting holes 180. While two nail targeting holes are shown, those skilled in the art would understand that a greater or lesser number of holes may be provided. As an example, the blocking screw locating holes 126 and the nail target holes 180 may be dimensioned to accept a typical outer drill sleeve 206 (best seen in FIG. 6). In the embodiment depicted in FIG. 3, the blocking screw locating holes 126 and the nail target holes 180 are about 10.5 millimeters in diameter.

Figure 4:
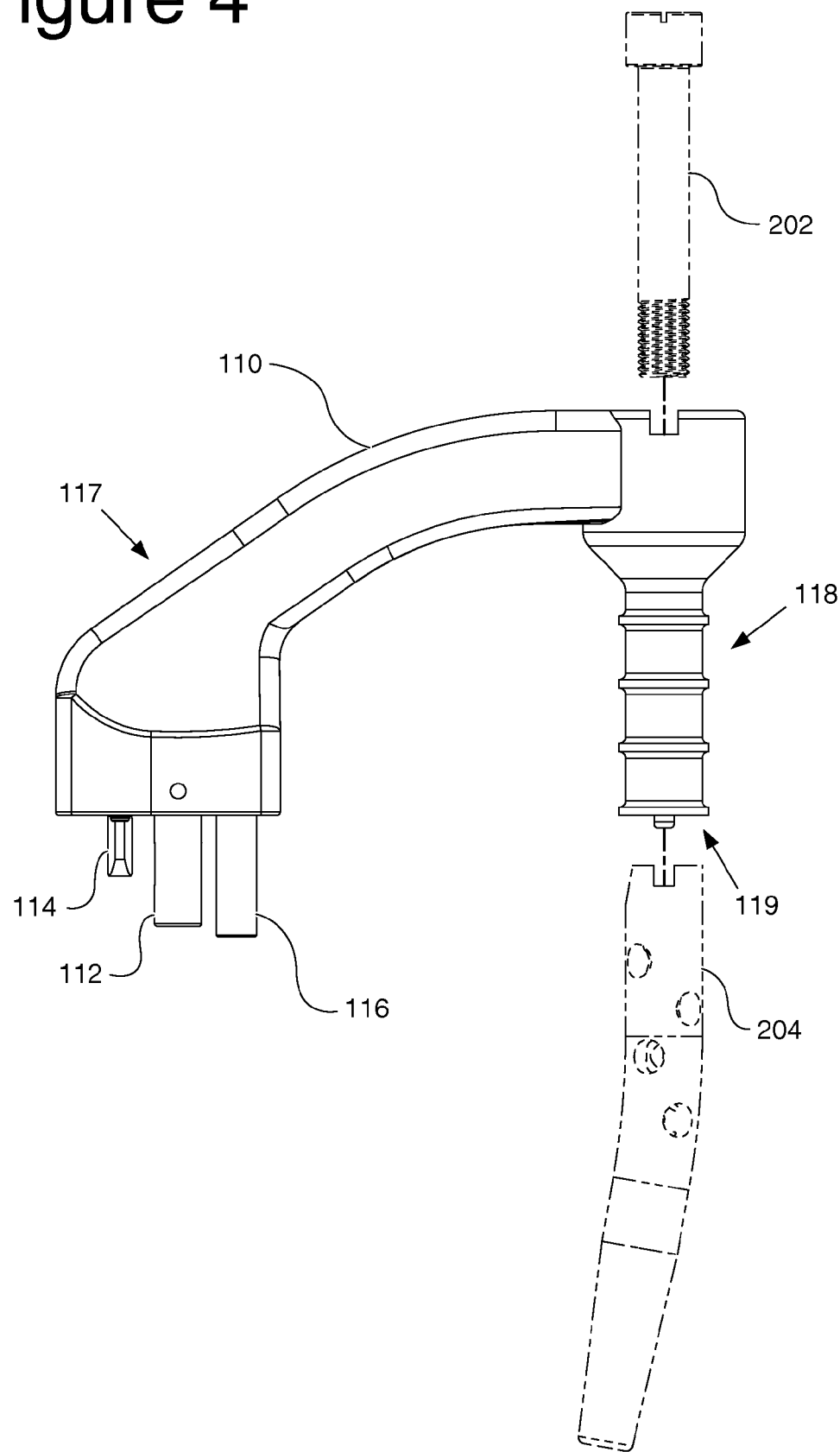
FIG. 4 is a side view of a mount.

FIG. 4 illustrates the mount 110. The mount 110 is adapted to connect to the intramedullary device 204, such as a trial or a nail, or to a reduction tool. A bolt or other fastener 202 may be used to connect the intramedullary device 204 to the mount 110. The mount 110 includes a neck portion 117 and a barrel portion 118. In the depicted embodiments, the barrel portion 118 is an integral part of the mount 110, but those skilled in the art would understand that the barrel portion could equally be a separate component. The barrel portion 118 connects to the intramedullary device 204 at a first end 119. The mount 110 also includes a first pin 112, a second pin 114, and a third pin 116. The pins 112, 114, 116 are used to align and connect the mount 110 to the frame 120. While pins are shown in the depicted embodiments, those skilled in the art would understand that other types of connectors or fasteners may be used.

The mount 110 is made from a rigid material. As examples, the mount 110 may be made from plastic or any medical grade metal, such as stainless steel, aluminum, or titanium. In some embodiments, a portion of the mount 110 is metal and another portion is plastic such that at least part of the mount 110 is radiolucent. As an example, the neck portion 117 may be made from plastic and the barrel portion 118 may be made of metal.

Figure 5:
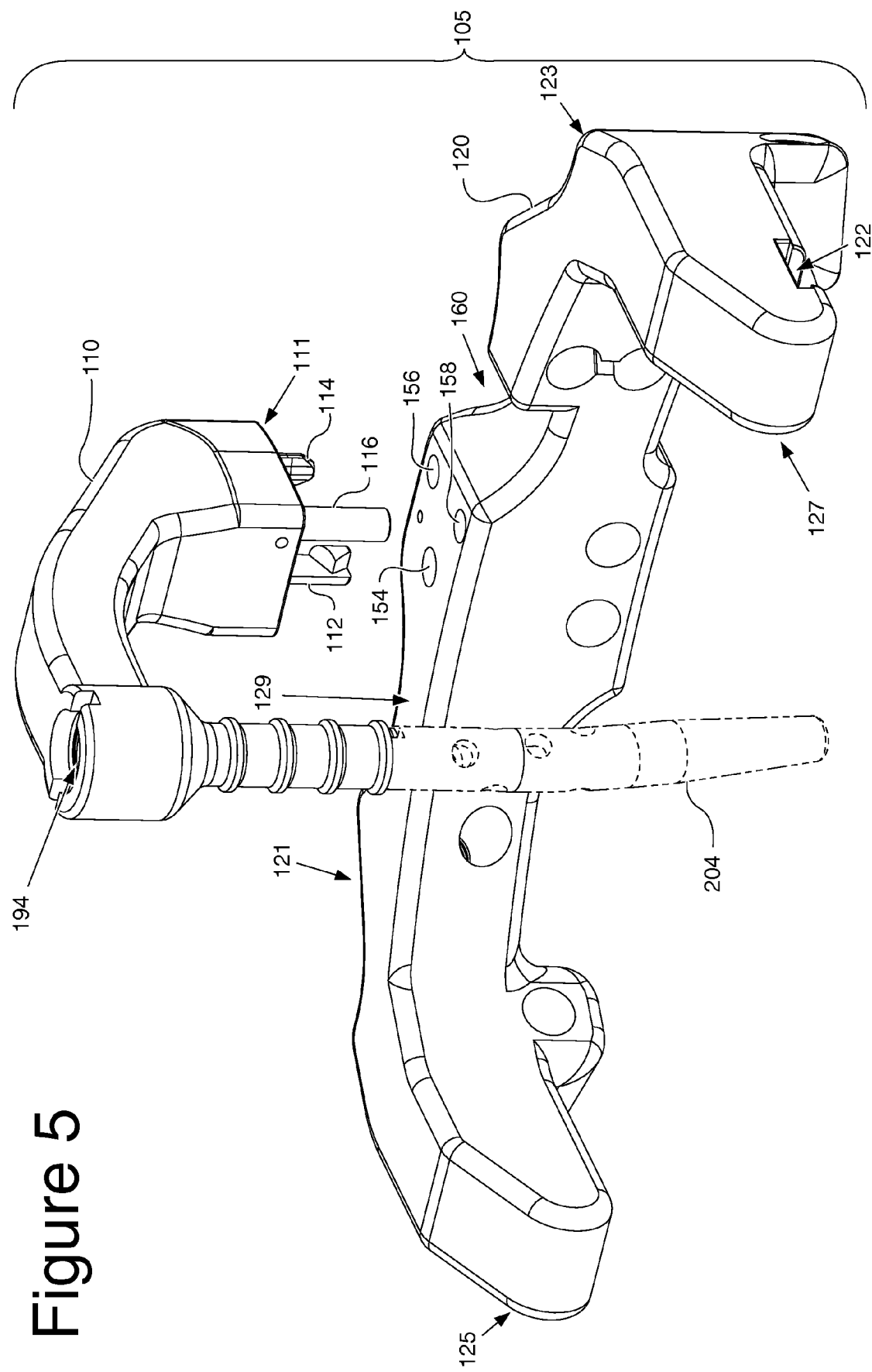
FIG. 5 is a perspective view of a drill jig.

FIG. 5 illustrates the mount 110 and the frame 120. As noted above, the mount 110 is removably attached to the frame 120. The assembly of the mount 110 to the frame 120 forms the drill jig 105. The frame 120 includes pin holes 154, 156, 158 to receive the respective pins 112, 114, 116. In other words, a first pin hole 154 corresponds to the first pin 112, a second pin hole 156 corresponds to the second pin 114, and a third pin hole 158 corresponds to the third pin 116. In the embodiment depicted in FIG. 5, the second pin 114 and the third pin 116 are used to align the mount 110 with the frame 120, and the first pin 112 is a locking pin and a locking mechanism (not shown) captures the first pin 112 when placed in the first pin hole 154. The pins 112, 114, 116 of the mount 110 slide within the pin holes 154, 156, 158 until a bottom surface 111 of the mount 110 contacts a top surface 129 of the frame 120. As the bottom surface 111 approaches the top surface 129, the locking mechanism engages to capture the first pin 112.

Optionally, the frame 120 may include one or more recess 160. In the embodiment depicted in FIG. 5, the recess 160 is located generally adjacent to where the mount 110 is attached to the frame 120 but other locations may be used. The recess 160 provides additional clearance, reduces the overall weight of the frame 120, and, in some cases, provides a hand rest for the surgeon.

Figure 6:
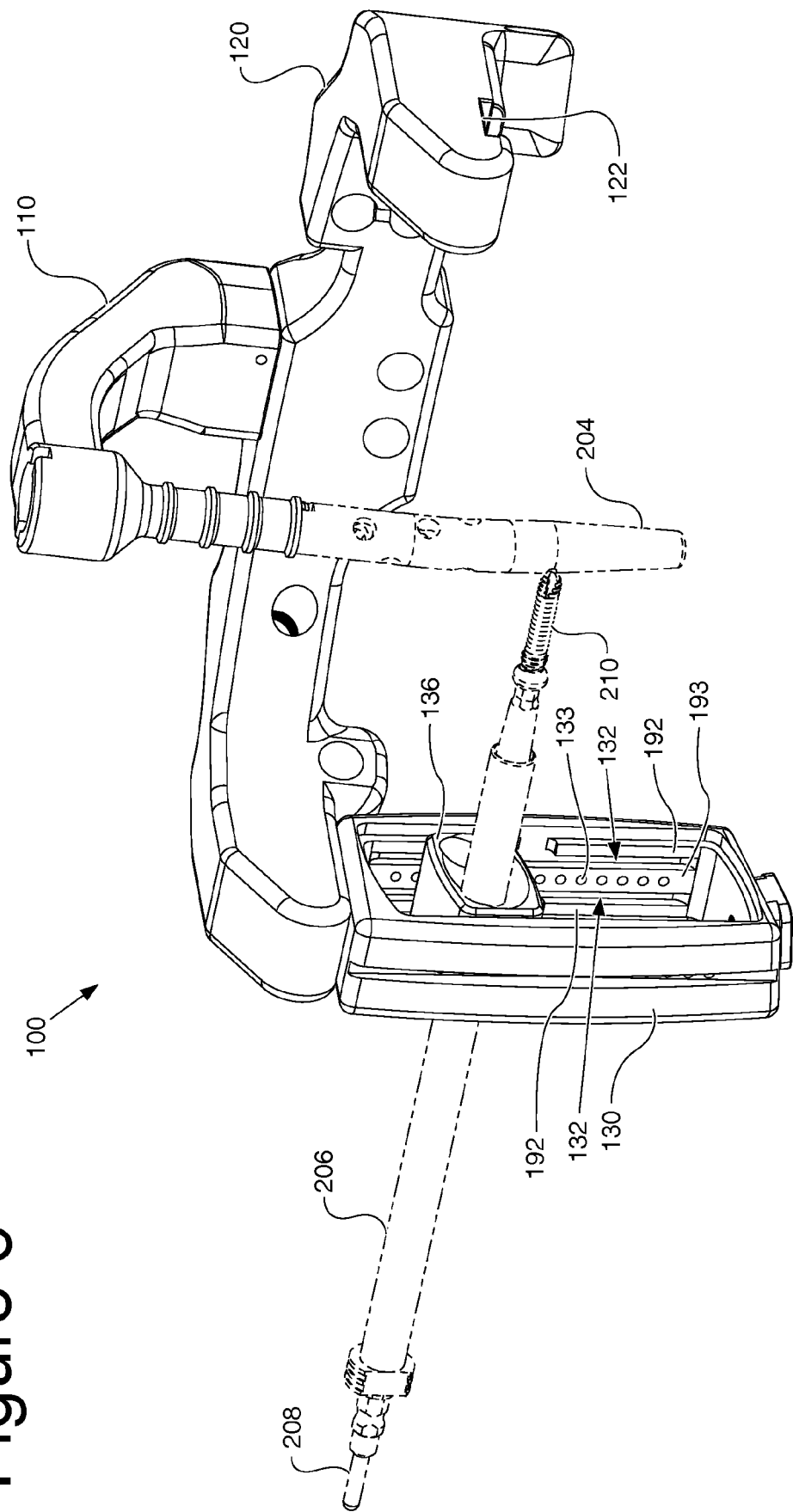
FIG. 6 is a perspective view of the second embodiment.

FIG. 6 illustrates the pilot member 130, which also may be termed a blocking screw attachment. In the depicted embodiments, the pilot member 130 is removably attached to the frame 120. However, the pilot member 130 also may be integrally formed as a portion of the frame 120. As examples, the pilot member 130 is made of plastic, a composite material, or other radiolucent material. The pilot member 130 is adapted to receive the cartridge 136. The cartridge 136 also may be termed a blocking screw cartridge. The cartridge 136 may also be made of plastic, a composite material, or other radiolucent material.

Figure 12:
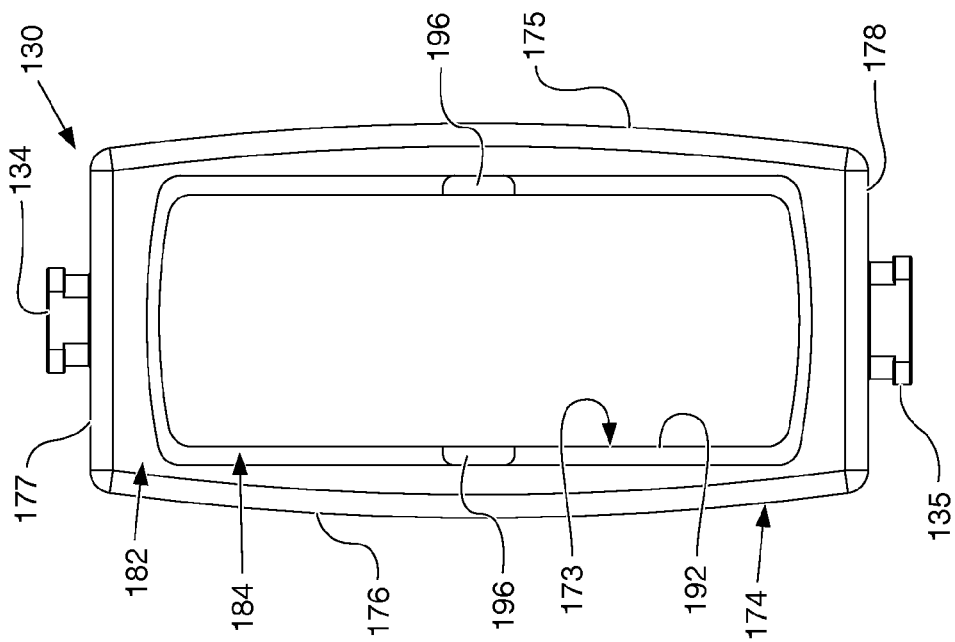
FIG. 12 is a front view of a pilot member in a first embodiment.

The cartridge 136 moves or slides in a longitudinal direction parallel to an imaginary long axis of the intramedullary device 204. The cartridge 136 includes at least one hole or an aperture for locating an axis of a blocking screw. In the embodiments depicted in FIGS. 9 and 10, the cartridge has two locating holes 137. However, the embodiment depicted in FIG. 11 has only one aperture 337. By moving the cartridge 136 within the pilot member 130, the axis of the blocking screw is located relative to the intramedullary device 204. In the depicted embodiments, the pilot member 130 has tracks 132, and the cartridge 136 slides along the tracks 132. The tracks 132 are formed by guide members 192 spaced apart from a center rib 193. As best seen in FIG. 12, the guide members 192 may include openings 196 to allow the cartridge 136 access to the tracks 132. Further, the tracks 132 have detents 133. The detents 133 are placed at regular intervals along the center rib 193. The cartridge 136 has a plunger 138 (best seen in FIGS. 7 and 8) on each side. The plungers 138 cooperate with the detents 133 to temporarily fix the cartridge in a location. In this manner, the cartridge 136 is slid along the tracks 132 and temporarily fixed in a position by engagement of each plunger 138 with one of the detents 133. By controlling the spacing between the detents 133, numerous positions of the cartridge 136 may be pre-selected. The spacing between the detents 133 may be in the order from about 2 millimeters to about ten millimeters. In the embodiment depicted in FIG. 6, the detents 133 have a spacing of about five millimeters between them.

FIGS. 7-10 illustrate a first embodiment of the cartridge 136. As best seen in FIGS. 7 and 8, the cartridge 136 includes a lip 139. The lip 139 engages the pilot member 130, such as a first planar surface 184 (best seen in FIG. 12), and limits travel of the cartridge 136 in a direction transverse to the longitudinal direction of the tracks 132.

As best seen in FIGS. 9 and 10, the cartridge 136 includes the locating holes 137. The locating holes 137 are dimensioned to accept a typical outer drill sleeve 206 (best seen in FIG. 6). In the embodiments depicted in FIGS. 9 and 10, the locating holes are about 10.5 millimeters in diameter.

The locating holes 137 are separated by a distance. The distance between the locating holes is dimensioned based upon the desired effect of the blocking screw. For example, if the blocking screw is used to direct the path of the nail or the fragment, then the hole spacing is selected such that blocking screw is inserted slightly offset from the center of the medullary cavity. Thus, the hole spacing depends upon the width of the medullary cavity. Further, only one of the blocking screw holes may be selected if the blocking screw is used to direct the path of the nail. The particular blocking screw hole is selected based upon the direction to which the nail or the fragment must be directed. On the other hand, if the blocking screw is used to enhance the stability of the intramedullary nail, then the hole spacing is selected such that the blocking screws are placed tangentially to the intramedullary nail. In this case, the hole spacing depends upon the diameter of the intramedullary nail.

In the embodiment depicted in FIG. 9, the center axis of each locating hole 137 is separated by a length LI. However, in a second embodiment depicted in FIG. 10, the center axis of each locating hole is separated by a length L2. Thus, the center axis of each locating hole 137 may be separated by a length L, wherein the length L may range from about five millimeters to about twenty-five millimeters. In the embodiment depicted in FIG. 10, the length LI is about five millimeters, and in the embodiment depicted in FIG. 10, the length L2 is about eighteen millimeters.

Alternatively, the spacing between holes 137 may be defined in terms of the nail size. For example, the spacing between an edge of each hole 137 may be defined in terms of the intramedullary nail diameter. Of course, most intramedullary nails are tapered, and, as such, the spacing may be defined in terms of the proximal diameter, the distal diameter, or the diameter of the main body shaft. As an example, if the main body shaft of the intramedullary nail has a diameter of thirteen millimeters, then the spacing would also be about thirteen millimeters or slightly larger. The spacing may be slightly larger to allow for tolerances in the nail, tolerances in the blocking screws, dimensional errors, or to allow the nail to translate slightly. It may also be desirable to have the spacing slightly smaller than the nail for an interference fit. Common nail sizes are 8.5 millimeters, 10 millimeters, 12 millimeters, and 13 millimeters. The instrument 100 includes modular cartridges that each have similar spacing between targeting holes. Thus, each modular cartridge has a spacing between the edges of each hole that corresponds to a common nail size (i.e., about 8.5 millimeters, about 10 millimeters, about 12 millimeters, and about 13 millimeters or slightly larger).

FIG. 11 illustrates a second embodiment of the cartridge, generally indicated by reference numeral 300. The cartridge 300 has a rotating drum 310 and the locating hole 337. Optionally, the rotating drum 310 may also include a handle 312. The rotating drum 310 has a center 314. The locating hole 337 is offset from the center 314 a fixed distance D. The distance D may be in the range from about one millimeter to about fifteen millimeters. In the embodiment depicted in FIG. 11, the distance D is about six millimeters. The rotating drum 310 allows a single cartridge to have multiple locations for the hole 337. The user rotates the rotating drum 310 using the handle 312 until the locating hole 337 reaches a selected location. The rotating drum 310 may be rotated clockwise or counter-clockwise. Optionally, the cartridge 300 may include markings MI, M2, M3, M4. The markings MI, M2, M3, M4 may specify the horizontal distance (relative to FIG. 11) from the center 314 to the center of the locating hole 337. Alternatively, the markings MI, M2, M3, M4 may specify the horizontal distance (relative to FIG. 11) from the center 314 to the edge of the locating hole 337.

Figure 13:
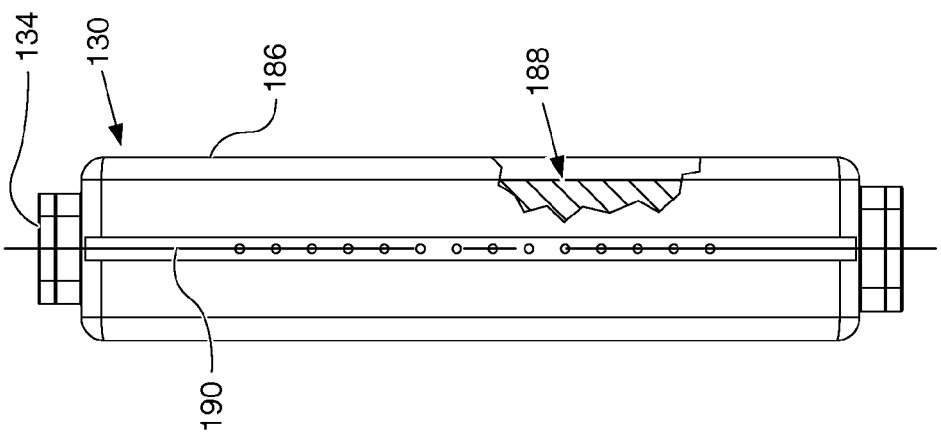
FIG. 13 is a side view of the pilot member shown in FIG. 12.

FIGS. 12 and 13 illustrate a first embodiment of the pilot member 130. As an example, the first embodiment may be used for a retrograde installation of a femoral intramedullary device. The pilot member 130 has an inner portion 173 and an outer portion 174. The inner and outer portion 173, 174 are formed by walls 175, 176, 177, 178. In other words, the pilot member 130 has a first wall 175, a second wall 176, a third wall 177, and a fourth wall 178. The second wall 175 is substantially parallel to the first wall 175. In the embodiment depicted in FIG. 12, the outer portion 174 of the first wall 175 and the second wall 176 is arcuate. The third wall 177 and the fourth wall 178 are substantially parallel to each other and substantially transverse to the first wall 175 and the second wall 176. The tracks 132 are located on the inner portion 173 along the first wall 175 and the second wall 176. As noted above, the guide members 192 may include openings 196 to allow the cartridge 136 access to the tracks 132.

The pilot member 130 also includes a first outer face 182 and the first planar surface 184. The first planar surface 184 is offset from the first outer face 182. This offset provides a ridge for the lip 139 of the cartridge 136. In other words, the lip 139 contacts first planar surface 184 and slides on this surface. The pilot member 130 also may include a second outer face 186 and a second planar surface 188. In some embodiments, the pilot member 130 may be mirrored about a center line 190 such that the pilot member 130 is reversible.

The pilot member 130 also includes a first stud 134. The first stud 134 is located on the outer portion 174 of the third wall 177. The first stud 134 is adapted to mate with the channel 122 of the frame 120. In some embodiments, the pilot member 130 may also include a second stud 135 located on the outer portion 174 of the fourth wall 178. The second stud 135 may be the same size and shape as the first stud 134 such that the pilot member 130 is reversible. Alternatively, the second stud 135 may have a different size and/or shape relative to the first stud 134.

Figure 14:
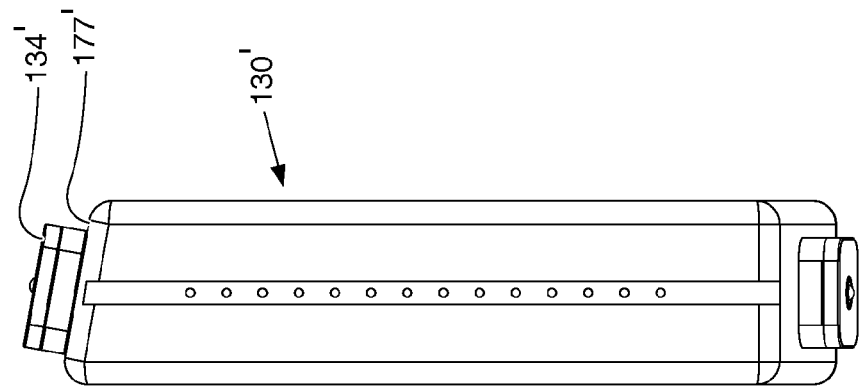
FIG. 14 is a front view of a pilot member in a second embodiment.
Figure 15:
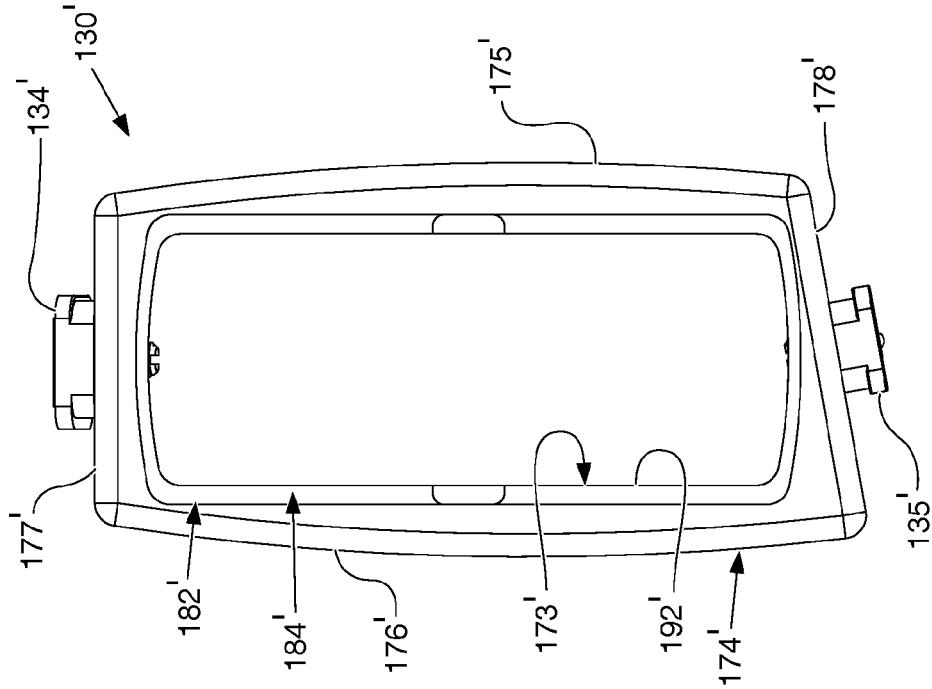
FIG. 15 is a side view of the pilot member shown in FIG. 14.

FIGS. 14 and 15 illustrate a second embodiment of the pilot member 130'. As an example the second embodiment may be used for an antegrade installation of a tibial intramedullary device. The pilot member 130' has an inner portion 173', an outer portion 174', a first wall 175', a second wall 176', a third wall 177', a fourth wall 178', a first outer face 182', and a first planar surface 184'. The second embodiment is similar to the first embodiment except the third wall 177' and the fourth wall 178' are angled to accommodate the relative angle of the tibial intramedullary device. The pilot member 130' also includes a first stud 134' and a second stud 135'.

Figure 16:
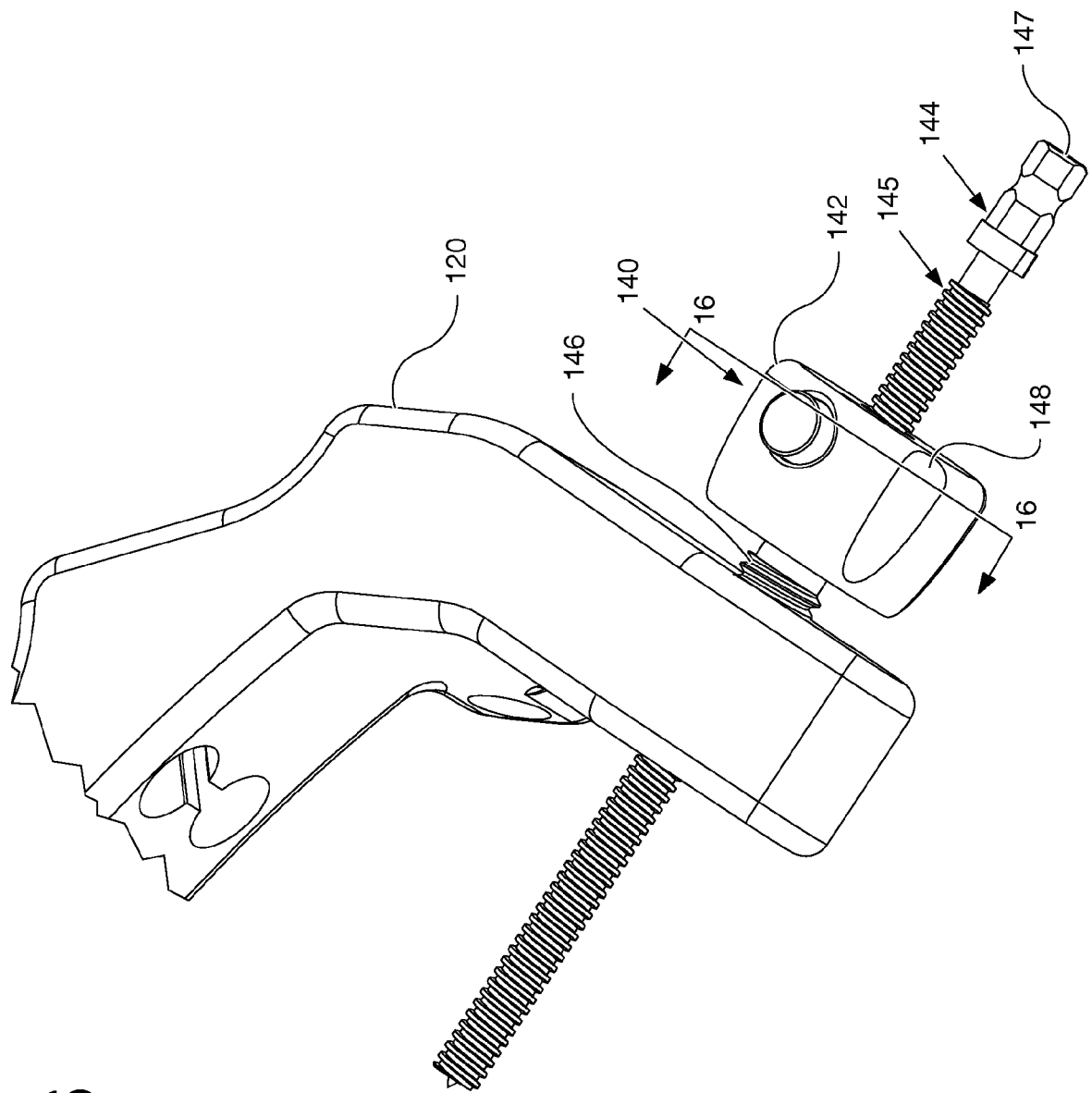
FIG. 16 is a perspective view of a fracture alignment device.

FIG. 16 illustrates a detailed view of the fracture alignment device 140. The fracture alignment device 140 includes a housing 142 and a screw shaft 144. The housing 142 includes an extension member 146 which threadingly engages the frame 120, such as by threading into the mounting hole 124. In some embodiments, the housing 142 also includes grip portions 148. The screw shaft 144 has a threaded portion 145 and a tip 147. As an example, the threaded portion 145 may have a diameter of about 6.4 millimeters. In the embodiment depicted in FIG. 16, the tip 147 has a hexagonal shape but other shapes may be used. What is significant is that the tip 147 is adapted for connection with a tool (not shown) such that a surgeon may use the tool to rotate the tip 147. The threaded portion 145 threads into a threaded hole 170 (best seen in FIGS. 17 and 18). As such, the screw shaft 144 moves axially when rotated.

Figure 18:
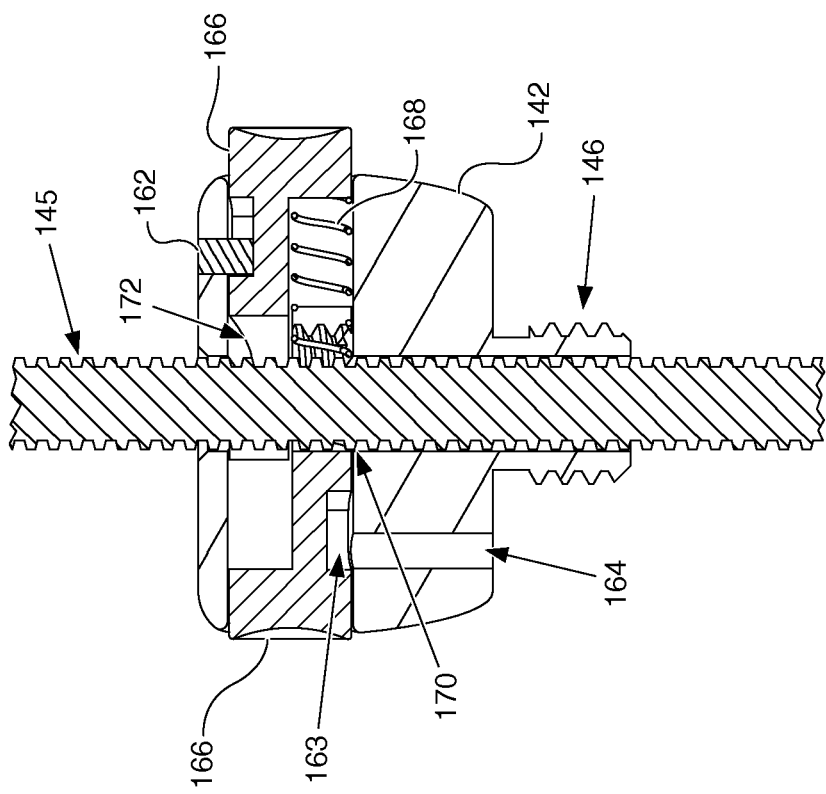
FIG. 18 is a sectional side view of the fracture alignment device shown in FIG. 17.
Figure 17:
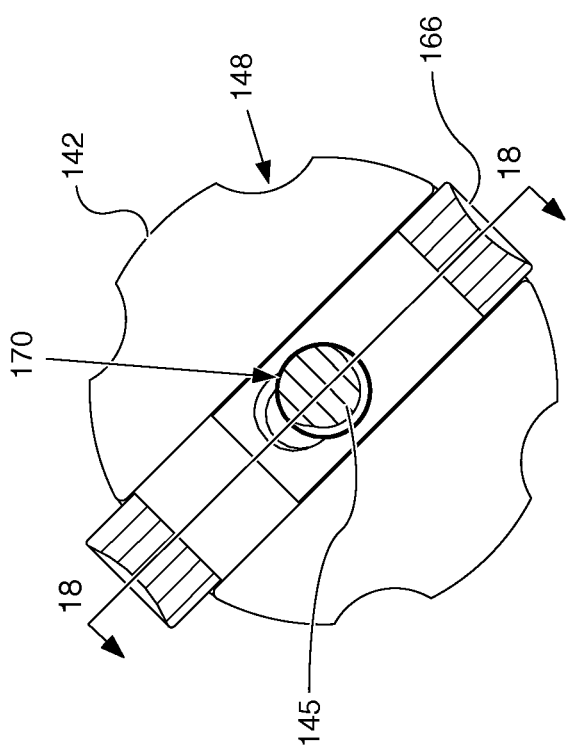
FIG. 17 is a sectional top view of the fracture alignment device shown in FIG. 16.

FIGS. 17 and 18 illustrate in greater detail the fracture alignment device 140. The fracture alignment device 140 includes buttons 166. As best seen in FIG. 17, the buttons 166 overlap and cooperate together. Each button 166 has a threaded hole 170 and a clearance hole 172. Springs 168 separate the buttons 166 and apply a spring force to bias each button 166 radially outward towards the housing 142. Each button has a slot or groove 163, and the housing 142 includes pin holes 164. A locking pin 162 is placed in the pin hole 164 and extends into the slot 163, thereby limiting the movement of each respective button 166. In a first position, the threaded holes 170 engage the threaded portion 145 of the screw shaft 144 of the fracture alignment device 140. As a user pushes upon the buttons 166, the buttons 166 move to a second position. In the second position, the threaded holes 170 disengage from the screw shaft 144 and the clearance holes 172 are proximate the screw shaft 144 such that the screw shaft 144 can easily be moved relative to the buttons 166. Thus, a surgeon can push the buttons 166 for gross movement of the screw shaft 144 and then release the buttons 166 and rotate the screw shaft 144 within the threaded holes 170 for fine adjustment of the screw shaft 144.

In operation, with respect to the first embodiment, a first step is to ream the proximal tibia fragment or distal femur fragment. A second step is to select the appropriate barrel 16. This is accomplished by estimating a length required for the barrel 16 and selecting a barrel with that length. A third step is to connect the instrument 10 to the intramedullary device 204 or a reduction tool. This step is achieved by attaching the barrel 16 of the mounting portion 12 to the intramedullary device 204. This may be done by engaging the fastener 202 with the barrel 16 and connecting the fastener 202 with the intramedullary device 204. The intramedullary device 204 is then inserted into the medullary cavity, if it has not been done already.

Optionally, the user may use the fracture alignment device 30 to manipulate the fragment by rotating the fracture alignment devices 31, 32, 34. The next step is to select an aperture 18, 22, 24, 25, 28, 29 for placement of the blocking screw 210. A location for the blocking screw 210 is selected through the surgeon's skill and judgment. The aperture 18, 22, 24, 25, 28, 29 is selected by choosing the aperture closest to the preferred location of the blocking screw 210. The next step is to install an outer drill sleeve 206 into the aperture 18, 22, 24, 25, 28, 29. Thereafter, the location of the aperture 18, 22, 24, 25, 28, 29 is verified through the use of an x-ray machine or image enhancer. If the aperture 18, 22, 24, 25, 28, 29 is not in the correct location, it may be necessary to adjust the instrument 10 by rotating the drill jig 11 relative to the intramedullary device 204 or by replacing the barrel 16 with a barrel having a different length. In other words, it may be necessary to replace the barrel 16 with one longer or shorter. If the barrel 16 has been changed or the drill jig 11 has been rotated, it will be necessary to repeat the verification step.

Once the outer drill sleeve 206 is in the correct location, the blocking screw pilot hole is drilled. A drill (not shown) is installed in the outer drill sleeve 206 and the bone is drilled. After the bone is drilled, the bone may be tapped. Next, the blocking screw is installed. The blocking screw 210 is attached to the end of a blocking screw wrench 208 (best seen in FIG. 6) and the blocking screw is screwed into the bone. This process may be repeated for the installation of additional blocking screws. The outer drill sleeve 206 is removed, and the instrument 10 is dismounted from the intramedullary device 204. If a trial has been used for the installation of blocking screws, then the trial would be removed with the instrument 10, and the instrument 10 may be used to insert the intramedullary nail into the reamed hole. Finally, the intramedullary nail is locked into place. In some embodiments, the instrument 10 may include holes for targeting the interlocking screws, and the instrument 10 is used to place the locking screws into the intramedullary nail.

As for the second embodiment, a first step is to connect the mount 110 to the intramedullary nail 204. This may be done by engaging the fastener 202 with the barrel portion 118 and connecting the fastener 202 with the intramedullary device 204. The frame 120 is releasably attached to the mount 110. In general, this is done after the mount 110 is attached to the intramedullary device 204, but the frame 120 equally could be attached to the mount 110 before connection to the intramedullary device 204. The cartridge 136, 300 is temporarily attached to the pilot member 130, and the pilot member 130 is temporarily attached to the frame 120. The order of these steps is not critical. The cartridge 136, 300 may be attached either before or after the pilot member 130 is attached to the frame 120. Moreover, the pilot member 130 may be attached to the frame 120 either before or after the frame 120 is attached to the mount 110.

The cartridge 136, 300 is attached to the pilot member by inserting the posts 131 into the openings 196 and sliding the posts 131 in the tracks 132 until the plungers 138 engages detents 133. A location for the blocking screw 210 is selected through the surgeon's skill and judgment. The aperture 126, 137, 337 is selected by choosing the aperture closest to the preferred location of the blocking screw 210. If the cartridge aperture 137, 337 is selected, the cartridge 136 is slid along the pilot member 130 until the aperture 137, 337 reaches the preselected location of the blocking screw 210.

Optionally, the user may use the fracture alignment device 140 to manipulate the fragment. The user mounts the fracture alignment device 140 to the frame 120 by inserting the extension member 146 into one of the mounting holes 124. Thereafter, the user manipulates the fragment by rotating the screw shaft 144.

Once the selected aperture is in the correct location, an outer drill sleeve 206 is inserted into the aperture 126, 137, 337. Thereafter, the location of the aperture 126, 137, 337 is verified through the use of an x-ray machine or image enhancer. If the aperture 126, 137, 337 is not in the correct location, it may be necessary to adjust the instrument 10 by rotating the frame 120 relative to the intramedullary device 204 or by sliding the cartridge 136, 300 relative to the pilot member 130. If adjustment was necessary, the verification step must be repeated. Once the outer drill sleeve 206 is in the correct location, the blocking screw pilot hole is drilled. A drill (not shown) is installed in the outer drill sleeve 206 and the bone is drilled. After the bone is drilled, the bone may be tapped. Next, the blocking screw is installed. The blocking screw 210 is attached to the end of a blocking screw wrench 208 (best seen in FIG. 6) and the blocking screw is screwed into the bone. This process may be repeated for the installation of additional blocking screws. Finally, the outer drill sleeve is removed, and the instrument 100 is dismounted from the intramedullary device 204.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. For example, while FIG. 5 illustrates the mount 110 being coupled to the frame 120 through the use of the locking pin 112, other structure and/or methods may be used to temporarily affix these items together. Thus, the breadth and scope of the present invention should not be limited by any of the above-described exemplary embodiments, but should be defined only in accordance with the following claims appended hereto and their equivalents.

What is claimed is:

1. A method of placing a blocking screw, the method comprising:
   connecting a mount to an intramedullary device;
   connecting a frame to the mount, thereby forming an assembled jig comprising the frame and the mount, wherein the frame comprises a first leg;
   attaching a cartridge to a pilot member, the cartridge having a cartridge aperture;
   attaching the pilot member to the frame at the first leg;
   selecting a location for a blocking screw using the cartridge and pilot member;
   drilling a blocking screw pilot hole; and
   installing the blocking screw;
   wherein with the intramedullary device connected to the mount of the assembled jig, at least a portion of the intramedullary device extends along a longitudinal axis, and the first leg extends from the mount in a first direction transverse to the longitudinal axis.

2. The method of claim 1, wherein the pilot member has an inner portion and an outer portion, the inner and outer portions formed by a first wall, a second wall, a third wall, and a fourth wall; and the cartridge is received within the inner portion of the pilot member, the cartridge having at least one locating hole, and wherein the cartridge moves within the pilot member.

3. The method of claim 1, further comprising the step of implanting the intramedullary device.

4. The method of claim 1, further comprising the step of verifying a location of the cartridge aperture using an imaging device.

5. The method of claim 1, further comprising the step of inserting a drill sleeve into the cartridge aperture.

6. The method of claim 1, further comprising the step of installing at least one other blocking screw.

7. The method of claim 1, further comprising the step of removing the mount and frame from the intramedullary device.

8. The method of claim 1, wherein the connecting the mount to the intramedullary device includes removably connecting the mount to the intramedullary device;
   wherein the connecting the frame to the mount includes removably connecting the frame to the mount;
   wherein the attaching the cartridge to the pilot member includes removably attaching the cartridge to the pilot member; and
   wherein the attaching the pilot member to the frame includes removably attaching the pilot member to the frame.

9. The method of claim 1, wherein the selecting the location for the blocking screw includes moving the cartridge within the pilot member to a position in which the cartridge aperture corresponds to a preselected location for the blocking screw, and inserting a drill sleeve into the cartridge aperture.

10. A method, comprising:
    removably coupling an intramedullary device to a barrel portion of a mount, wherein the mount includes the barrel portion and a neck portion, and at least a portion of the intramedullary device extends along a first longitudinal axis;
    removably attaching a frame to the neck portion of the mount, the frame having a first leg and a second leg, wherein the first leg and the second leg extend from the mount in opposite directions when the frame is attached to the mount;
    removably attaching a pilot member to the frame at a selected one of the first and second legs, wherein a cartridge including a locating hole is movably received within an inner portion of the pilot member;
    selecting a location for a blocking screw;
    moving the locating hole to a target position corresponding to the location selected for the blocking screw, wherein moving the locating hole includes moving the cartridge within the pilot member in a first direction substantially parallel to the first longitudinal axis; and securing the cartridge to the pilot member with the locating hole in the target position.

11. The method of claim 10, further comprising inserting a drill sleeve into the locating hole, extending a drill through the drill sleeve, and forming a blocking screw pilot hole with the drill.

12. The method of claim 11, further comprising installing the blocking screw in the blocking screw pilot hole.

13. The method of claim 12, further comprising extending a blocking screw wrench through the drill sleeve, wherein the installing includes screwing the blocking screw into the blocking screw pilot hole with the blocking screw wrench.

14. The method of claim 10, wherein the inner portion of the pilot member includes a pair of tracks extending in the first direction, the cartridge is movably coupled to the tracks, and moving the cartridge includes moving the cartridge along the tracks.

15. The method of claim 14, wherein the pilot member includes a plurality of detents, the cartridge includes a plunger operable to selectively engage the detents, and securing the cartridge to the pilot member includes engage the plunger with one of the detents.

16. A method, comprising:
removably coupling an intramedullary device to a barrel portion of a mount, wherein the mount includes the barrel portion and a neck portion, and at least a portion of the intramedullary device extends along a first longitudinal axis;
removably attaching a frame to the neck portion of the mount, the frame having a first leg and a second leg;
removably attaching a pilot member to the frame at the first leg, wherein a cartridge including a locating hole is movably received within an inner portion of the pilot member;
selecting a location for a blocking screw;
moving the locating hole to a target position corresponding to the location selected for the blocking screw, wherein moving the locating hole includes moving the cartridge within the pilot member in a first direction substantially parallel to the first longitudinal axis; and
securing the cartridge to the pilot member with the locating hole in the target position;
wherein the cartridge includes a rotatable drum, the locating hole is formed in the drum and is offset from a rotational axis of the drum, and moving the locating hole further includes rotating the drum about the rotational axis.

17. A method, comprising:
removably coupling an intramedullary device to a barrel portion of a mount, wherein the mount includes the barrel portion and a neck portion, and at least a portion of the intramedullary device extends along a first longitudinal axis;
removably attaching a frame to the neck portion of the mount, the frame having a first leg and a second leg;
removably attaching a pilot member to the frame at the first leg, wherein a cartridge including a locating hole is movably received within an inner portion of the pilot member;
selecting a location for a blocking screw;
moving the locating hole to a target position corresponding to the location selected for the blocking screw, wherein moving the locating hole includes moving the cartridge within the pilot member in a first direction substantially parallel to the first longitudinal axis; and
securing the cartridge to the pilot member with the locating hole in the target position;
wherein the second leg includes a mounting hole, the method further comprising:
coupling a housing including an opening to the second leg with the opening aligned with the mounting hole;
passing a shaft through the opening and the mounting hole, the shaft having an end and a tip; and
manipulating a bone fragment with the end of the shaft.

18. The method of claim 17, wherein the housing further includes an extension member, the opening extends through the extension member, and coupling the housing to the second leg includes engaging external threads of the extension member with internal threads of the mounting hole.

19. The method of claim 17, wherein the shaft defines a second longitudinal axis and includes a first threaded portion, and a button including a second threaded portion is movably coupled to the housing, the method further comprising:
finely adjusting an axial position of the shaft, the finely adjusting including placing the button in a first position in which the first and second threaded portions are engaged with one another, and rotating the shaft about the second longitudinal axis, wherein the engaged first and second threaded portions axially move the shaft in response to the rotating; and
grossly adjusting the axial position of the shaft, the grossly adjusting including placing the button in a second position in which the first and second threaded portions are disengaged from one another, and moving the shaft along the second longitudinal axis.

20. The method of claim 19, wherein the tip of the shaft is configured for connection with a tool, and manipulating the bone fragment includes placing the button in the first position, connecting the tool to the tip of the shaft, and rotating the shaft with the tool, thereby moving the shaft and the bone fragment in a direction of the second longitudinal axis.

21. The method of claim 1, wherein in the assembled jig, the first leg further extends in a second direction transverse to the first direction and the longitudinal axis.

22. The method of claim 21, wherein the frame further comprises a second leg,
wherein the pilot member is selectively attachable to each of the first and second legs, and
wherein in the assembled jig, the second leg extends in the second direction, and further extends in a third direction opposite the first direction.

23. The method of claim 22, wherein in the assembled jig, the mount extends from the frame in a direction along the longitudinal axis, and further extends in the second direction.

24. The method of claim 1, wherein in the assembled jig, the mount extends from the frame in a direction along the longitudinal axis.

25. The method of claim 24, wherein the mount comprises a barrel portion and a neck portion, wherein connecting the mount to the intramedullary device comprises connecting the barrel portion to the intramedullary device, and wherein in the assembled jig, the neck portion of the mount extends from the frame in the direction along the longitudinal axis.

26. The method of claim 10, wherein removably attaching the pilot member to the frame includes mounting the pilot member on only the selected one of the first and second legs.

27. The method of claim 10, wherein a plane is defined through the first and second legs, and wherein with the intramedullary device coupled with the mount and the mount attached to the frame, the intramedullary device extends through the plane.

28. The method of claim 10, wherein with the frame attached to the mount, the first and second legs extend along a plane transverse to the longitudinal axis.

\* \* \* \* \*